United States Patent [19]

Facal Garcia

[11] Patent Number: 4,577,627

[45] Date of Patent: Mar. 25, 1986

[54] ANTERIOR TRACTION MYOTATIC CHIN STRAP FOR THE TREATMENT OF MANDIBULAR RETROGNATHISM

[76] Inventor: Antonio Facal Garcia, Gran Via, 50-1°, Vigo, Spain

[21] Appl. No.: 564,551

[22] Filed: Dec. 22, 1983

[30] Foreign Application Priority Data

Apr. 18, 1983 [ES] Spain .................................... 521.582

[51] Int. Cl.⁴ ........................................... A61F 5/08
[52] U.S. Cl. ..................................... 128/76 R; 433/5
[58] Field of Search .................... 128/89 A, 163, 164, 128/76 R, 75; 433/5; 272/94

[56] References Cited

U.S. PATENT DOCUMENTS

| | | | |
|---|---|---|---|
| 3,401,457 | 9/1968 | Hickham | 433/5 |
| 4,212,637 | 7/1980 | Dougherty et al. | 433/5 |
| 4,375,355 | 3/1983 | Dahan | 433/5 |
| 4,375,962 | 3/1983 | DeWoskin | 433/5 |

FOREIGN PATENT DOCUMENTS

581089 7/1933 Fed. Rep. of Germany .......... 433/5

*Primary Examiner*—Richard J. Apley
*Assistant Examiner*—H. Macey
*Attorney, Agent, or Firm*—Wenderoth, Lind & Ponack

[57] ABSTRACT

An anterior traction myotatic chin strap treats mandibular retrognathism by exciting the myotatic reflex action of mandibular advance, thereby producing the best conditions to stimulate the forward growth of the mandible to a maximum, this being the first objective in the treatment of mandibular retrognathism or Skeletal Class II Malocclusion, in which a poor mandibular growth in relation to the growth of the upper maxilla in the anteroposterior direction, is produced. The myotatic chin strap, due to its support on the labiomenton groove and due to its backwards and slightly downwards component force by means of a band placed behind the neck and which is joined to the lower arms of the chin strap by smooth rubber bands, excites the myotatic or stretch reflex of the muscles which advance and close the mandible, maintaining a functional position in the advance and closure of the mandible as a reflex reaction to the applied backwards and slightly downwards pull, provided that the intensity of this pull is minimum. The myotatic chin strap, through its upper arms connected to other smooth elastic bands, can exert a pull on an orthodontic or orthopedic apparatus placed in the patient's mouth to correct the defects of his teeth, wherefore the teeth will occupy a more anterior position at the end of the treatment, thereby obtaining the best therapeutic results.

4 Claims, 4 Drawing Figures

ANTERIOR TRACTION MYOTATIC CHIN STRAP FOR THE TREATMENT OF MANDIBULAR RETROGNATHISM

BACKGROUND OF THE INVENTION

The present invention relates to an anterior traction myotatic chin strap for the treatment of mandibular retrognathism.

Mandibular retrognathism or Skeletal Class II malocculsion is a syndrome which is characterized by the poor growth of the mandible, in relation to the growth of the upper maxilla in an antero-posterior direction. Its treatment is based on the use and increase of the growth of the mandible. According to the most modern studies, two essential conditions, among others, are required to achieve this growth.

1. An exercise for manidublar advance should be practised.
2. The position of the teeth should be as far forward as possible, at the end of the treatment.

Up to now, mandibular advance was induced by using bimaxillary orthopedic apparatus, such as activator. However, this device, as well as all other therapeutic means used at present time, produce a final positioning of the teeth which is too far backwards. This secondary effect is undesirable since it clearly inhibits mandibular growth and therefore is contrary to the objective of the treatment. That is to say, these apparatus only comply with the first of the two conditions.

SUMMARY OF THE INVENTION

With the application of the anterior traction myotatic chin strap according to the invention, a greater mandibular growth can be obtained, since it represents the first apparatus which recognizes the two essential conditions:

1. The myotatic reflex action of mandibular advance is excited.
2. At the end, a most anterior positioning of the teeth is obtained, since they are pulled forward.

The anterior traction myotatic chin strap is designed to be used as a complement of active or functional intrabucal apparatus, which in turn corrects defects of the teeth, its main feature being the combined used with an activator or other existing functional bimaxillary apparatus, extraordinarily improving the therapeutic results.

The anterior traction myotatic chin strap constitutes an orthopedic apparatus for the treatment of mandibular retrognathism, during which, on the one hand, mandibular growth is stimulated by the reflex excitation of the muscles which advance and close the mandible. In order to achieve this, it is necessary to pull the chin slightly and continuously downwards and backwards, by means of a band embracing the posterior part of the neck of the patient and rubber bands which joint such band to the chin strap itself. On the other hand, there are other bands joining the strap to the corrector placed in the set of teeth of the patient since, as mentioned, the chin strap of the invention has been designed to be used as a complement of other intrabucal apparatus, with the purpose of pulling them forwards.

The immediate reflex action produced, known as myotatic or stretching reflex, consists in adopting, in an involuntary and maintained manner, a position of the mandible which is opposite to the direction of the applied pull, i.e. the mandible tends to close and to advance in such a way that daily repetition of this exercise activates mandibular growth.

This therapeutic idea of utilizing a myotatic reflex action to stimulate mandibular growth is completely original, in spite of being based on an elemental physiological fact and of being readily applied in clinics.

Besides the aforesaid, it should be pointed out that the true utility of the anterior traction myotatic chin strap of the invention in that it is a new and necessary complement in bimaxillary apparatus for dentomaxillary orthopedics, such as an activator, which are widely used in the world today to treat mandibular retrognathism or skeletal Class II malocclusion. Absolutely all these apparatus produce, apart from mandibular advance, a secondary effect of displacing the set of teeth backwards and downwards, causing a reflex inhibition of mandibular growth, contrary precisely to the objectives of the treatment.

Thus, the myotatic chin strap of the invention prefectly and simply overcomes the undesirable effects of the activator through its forwards and upwards traction mechanism, when both apparatus are jointly applied to the patient.

Structurally, the myotatic chin strap of the invention basically comprises the association of three main parts, one of which comprises a central body made of a plastic material whose nature is such that it is neither toxic nor irritating to the skin. This body adopts an elongated, slightly flat shape, provided with a small curvature which allows it to adapt anatomically to the labiomenton groove.

The central body should be thick enough to allow the other two parts of the strap to be embedded therein. These parts are in the form of outwardly protruding wire-like elements forming pairs of upper and lower arms.

The upper arms protrude parallel to one another, are directed upwards and forwards, and have, at approximately half of their length, slight bend from which they project slightly upwards, thereby to space the arms from the lower lip, and end in respective loops to which an elastic band may be hooked.

The lower arms protrude laterally opposite sides of the central plastic body, are directed downwards and backwards, curving inwards to adapt to the shape of the body of the mandible, and end in respective loops to which an elastic band will be hooked.

With this construction, the myotatic chin strap of the invention will adapt perfectly to the anatomy of the corresponding application zone, the central plastic body being placed on the labiomenton groove, while the curved lower arms will adapt to the sides of the lower mandible, so that elastic bands hooked in their corresponding loops are joined to a fastening strip which will be arranged about the posterior part of the patient's neck.

The upper arms will be arranged in front of lips of the patient, so that the elastic bands provided in their end loops are hooked to an intrabucal apparatus placed in the set of teeth of the patient.

Hence, the thusly constructed chin strap will pull the set of teeth forwards and upwards, the selected and sole point of support thereof being the labiomenton groove.

It should be emphasized that the chin straps presently existing in the market are designed to treat mandibular prognathism, exerting a pull, from the head, upwards and backwards. Thus, when supported on the chin they are maintained perfectly in place.

The myotatic chin strap is the first to be used to obtain a contrary effect, that is for the treatment of the contrary syndrome or mandibular retrognathism, therefore constituting a chin strap which will be subject to a force component which, in function, tends to displace it downwards. This can only be prevented by supporting it on the labiomenton groove.

Summing up, it can be stated that the conventional chin traps are designed so that an upward force can be applied thereon, whereas the chin strap of the invention is the only one on which it is possible to apply a downward force, due, precisely, to its support on the labiomenton groove. Hence, it is impossible to use it to apply thereon an upward force.

Referring to the practical advantages of the chin strap of the invention, the following can be stated:

Both the idea of myotatic excitation and its practical application by means of a chin strap, as well as its forwards and upwards traction effect on the set of teeth during treatment of skeletal Class II malocclusion or mandibular retrognathism, represent a therapeutic revolution within dento-maxillary orthopedics, in the sense that, up to now many of these treatments were carried out with poor results, since, during the normal treatment, a backward and downward displacement of the teeth was produced, leading to poor therapeutic results. Due to this, the orthopedic bimaxillary apparatus are really effective in only a low percentage of treated cases.

However, if the effect of such orthopedic apparatus is complemented with the chin strap of the invention, mandibular retrognathism can be treated with complete success, even in the most difficult cases, substantially reducing the duration and cost of the treatment.

BRIEF DESCRIPTION OF THE DRAWINGS

The following description will provide a better understanding of the characteristics of the invention, with reference to the accompanying drawings, wherein.

DETAILED DESCRIPTION OF THE INVENTION

Figure 1:
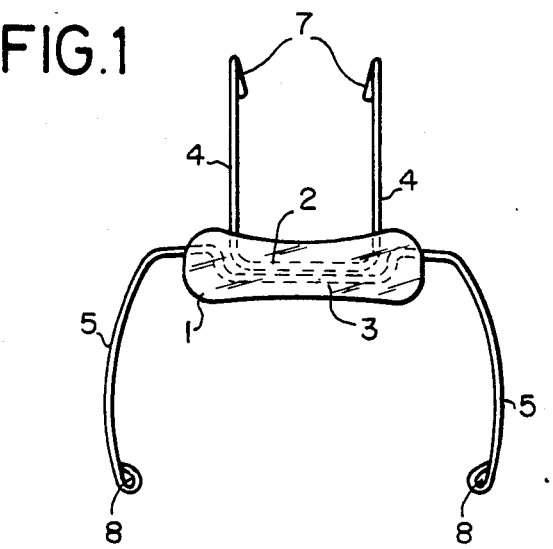
FIG. 1 is a front view of the myotatic chin strap made in accordance with the invention.
Figure 2:
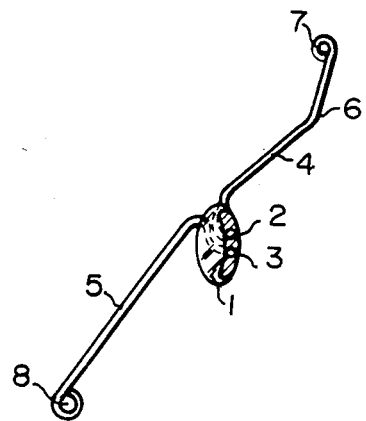
FIG. 2 is a side view of the chin strap illustrating the profile of wire arms thereof which protrude from a central plastic body thereof.

Referring to these figures, the myotatic chin strap for the treatment of mandibular retrognathism according to the invention includes a slightly rectangular, flat piece 1 made of a plastic material which is neither toxic nor irritating to the skin of the patient. Piece 1 has a slight curvature which enables it to adapt anatomically to the labiomenton groove of the patient.

Piece 1 is thick enough to allow two wire-like elements 2 and 3 to be embedded therein. These elements protrude outwards to define pairs of arms 4 and 5. The wire element or elements 2 defining protruding arms 4 is or are slightly thinner than the wire element or elements 3 defining arms 5.

Figure 4:
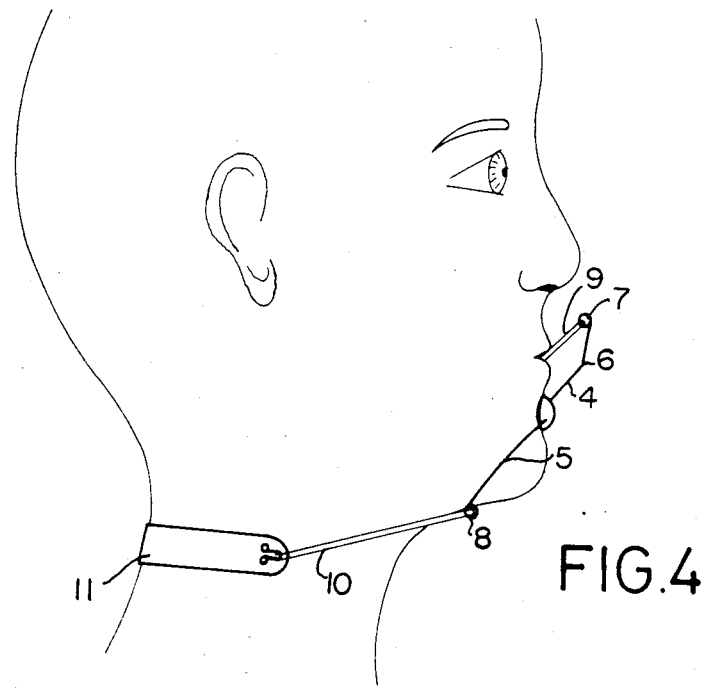
FIG. 4 is a side view of the application of the myotatic chin strap to a patient, representing a perfect adjustment thereof to the labiomenton groove.

The upper arms 4 project parallel to one another and are directed upwards and forwards, as can be clearly seen in FIG. 4, in such a way that at approximately half their length there is a slight bend from which arms 4 project upwards. Bands 6 space arms 4 from the patient's lower lip.

The arms 5 formed by wire element 3 are considered as the lower arms and protrude from the plastic piece 1 downwards and backwards, following an inwardly curved profile to adapt to the body of the mandible.

Both the arms 4 and the arms 5 end in respective loops 7 and 8 to which corresponding elastic elements 9 and 10, respectively, will be hooked.

Figure 3:
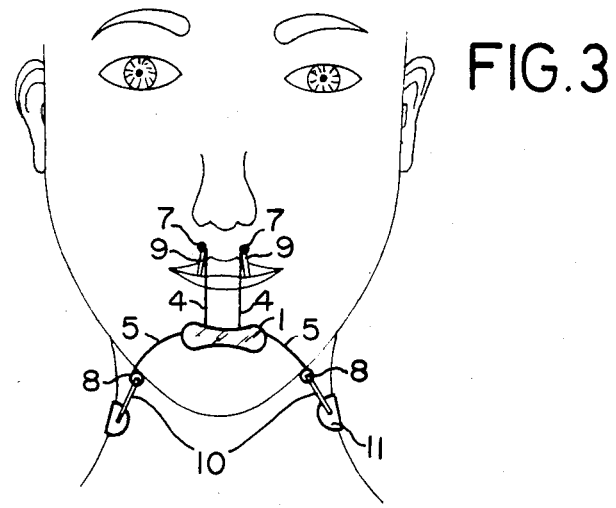
FIG. 3 is a front view of the application of the chin strap to a patient, representing elastic elements which join the upper arms to other apparatus, both orthodontic and bimaxillary for dentomaxillary orthopedics, used simultaneously by the patient, as well as elastic elements which join the lower arms to a strap which is adapted to extend around the back and sides of the neck of the patient.

The application of the chin strap to the patient will take place as follows:

Piece 1 will be placed on the labiomenton groove of the patient, as illustrated in FIGS. 3 and 4, in such a way that the arms 4 will be projected upwards in front of the lips of the patient, while the lower arms 5 will adapt laterally to the lower mandible. A strap 11, which will be arranged and adapted to the posterior lateral part of the patient's neck will be hooked to the elastic elements 10 which are hooked, in turn, to the loops 8, as shown in FIG. 4.

Thus, in view of the pull exerted by the elastic elements 10 joined to the strap 11, the chin strap will exert a backward and slightly downward pull on the mandible, producing an immediate reflex action, called myotatic or stretching reflex, and which consists in adopting, in an involuntary and maintained manner, a position of the mandible which is opposite to the direction of the applied pull. In other words, the mandible will tend to advance and to close, thereby stimulating the growth thereof.

Furthermore, due to their position or orientation, the elastic elements 9, hooked to the upper arms 4, will pull the set of teeth forwards and upwards, counteracting the secondary and undesirable effect of displacing the set of teeth backwards and downwards, caused by the known dento-maxillary orthopedic apparatus.

I claim:

1. An anterior traction myotatic appliance for the treatment of mandibular retrognathism or Skeletal Class II malocclusion, said appliance comprising:
   a generally flat member anatomically configured to fit in the labiomenton groove of a patient;
   a band to be applied around the back of the neck of the patient and connected to said member by means for causing, in cooperation with said band, said member to impart to the lower mandible of the patient a rearward and downward force, thereby causing excitation of the myotatic reflex action mandible advance wherein the muscles of the lower mandible stretch against said force and promote forward mandible growth; and
   further means, extending from said member in a direction substantially opposite that of said first mentioned means and adapted to be connected to a conventional orthodontic appliance adapted to be inserted in the mouth of the patient, for imparting to the teeth of the patient a forward and upward force, thereby positioning the teeth favorably with respect to the position of the mandible at the end of treatment after said forward mandible growth.

2. An appliance as claimed in claim 1, wherein said member comprises a single piece of material having a curvature to fit said labiomenton groove of the patient, said means for causing said member to impart a rearward and downward force comprises a pair of lower arms of wire-like material extending downwardly and rearwardly from said member, each said lower arm having a curvature adapted to the shape of said lower mandible of the patient and having at a free end thereof a hook, and elastic elements attaching respective ends of said band to said hooks, and said means for imparting forward and upward force to said teeth of the patient comprises a pair of upper arms of wire-like material extending upwardly and forwardly from said member, each said upper arm having a hooked free end, and elastic elements attaching respective said hooked free ends to the orthodontic appliance.

3. An appliance as claimed in claim 2, wherein said upper and lower arms are embedded in the material of said member.

4. An appliance as claimed in claim 2, wherein said single piece is formed of a plastic material which is neither toxic nor irritating to the skin of the patient.

* * * * *